(12) United States Patent
Tanaka et al.

(10) Patent No.: US 8,501,482 B2
(45) Date of Patent: Aug. 6, 2013

(54) APPARATUS FOR ANALYZING PARTICLES IN URINE AND METHOD THEREOF

(75) Inventors: Yousuke Tanaka, Kobe (JP); Junya Inoue, Ono (JP); Masatsugu Ozasa, Kobe (JP); Yasuyuki Kawashima, Kobe (JP)

(73) Assignee: Sysmex Corporation, Kobe (KP)

( * ) Notice: Subject to any disclaimer, the term of this patent is extended or adjusted under 35 U.S.C. 154(b) by 941 days.

(21) Appl. No.: 11/798,066

(22) Filed: May 10, 2007

(65) Prior Publication Data

US 2009/0050821 A1  Feb. 26, 2009

(30) Foreign Application Priority Data

May 17, 2006 (JP) .................. 2006-137511

(51) Int. Cl.
*G01N 33/48* (2006.01)
(52) U.S. Cl.
USPC .............. 436/63; 436/43; 436/47; 436/49; 436/52; 436/55; 436/166
(58) Field of Classification Search
None
See application file for complete search history.

(56) References Cited

U.S. PATENT DOCUMENTS

| | | | |
|---|---|---|---|
| 5,325,168 | A | 6/1994 | Nakamoto et al. |
| 6,118,522 | A | 9/2000 | Kanai et al. |
| 2002/0076743 | A1 | 6/2002 | Sakai et al. |
| 2003/0032193 | A1 | 2/2003 | Narisada |
| 2003/0143117 | A1 | 7/2003 | Nagai et al. |
| 2006/0073601 | A1 * | 4/2006 | Kawashima et al. ........... 436/63 |

FOREIGN PATENT DOCUMENTS

| | | |
|---|---|---|
| EP | 0 515 099 A | 11/1992 |
| EP | 1 089 078 A | 4/2001 |
| EP | 1 136 563 A | 9/2001 |
| EP | 1 136 563 A2 | 9/2001 |
| EP | 1 405 918 A | 4/2004 |
| EP | 1 574 839 A | 9/2005 |
| EP | 1 840 577 A | 10/2007 |
| JP | 8-170960 A | 7/1996 |
| JP | H09-329596 | 12/1997 |
| JP | 11-023446 A | 1/1999 |
| JP | 2006-017555 A | 1/2006 |

OTHER PUBLICATIONS

Higashino, et al. Urinalysis and Frontier Technology Full-Automated Urinary Formed Element Analyzer UF-100, Med. Technol., 20, 9, 2004, additiona vol. (September), p. 137-142, Full English Translation.

* cited by examiner

*Primary Examiner* — Dirk Bass
(74) *Attorney, Agent, or Firm* — Sughrue Mion, PLLC

(57) ABSTRACT

An apparatus, intended for use in analyzing particles in urine is disclosed, that comprising: a sample distribution section for distributing urine samples to a first aliquot and a second aliquot; a first specimen preparing section for preparing a first specimen for measuring urinary particles, containing at least erythrocytes, by mixing a first stain reagent and the first aliquot; a second specimen preparing section for preparing a second specimen for measuring bacteria by mixing a second stain reagent and the second aliquot; and an optical detecting section comprising a light source for irradiating a light to a specimen being supplied, a scattered light receiving element for detecting scattered light emitted from the specimen, and a fluorescence receiving element for detecting fluorescence emitted from the specimen. A method intended for use in analyzing particles in urine is also disclosed.

9 Claims, 13 Drawing Sheets

APPARATUS FOR ANALYZING PARTICLES IN URINE AND METHOD THEREOF

CROSS-REFERENCE TO RELATED APPLICATIONS

This application claims priority from Japanese Patent Application 2006-137511 filed on May 17, 2006, the disclosure of which is herein incorporated by reference in its entirety.

FIELD OF THE INVENTION

The present invention relates to an apparatus for analyzing particles in urine and method thereof, and more specifically to an apparatus for analyzing particles in urine for optically measuring and analyzing constituents contained in urine with the use of flow cytometry.

BACKGROUND

General measurement items of particles in urine include erythrocytes, leukocytes, epithelial cells, casts and bacteria. Of these, the cast is produced in such a manner that Tomm-Horsfall mucoproteins clotted and precipitated in the renal tubule lumen under the presence of a small amount of plasma protein (albumin) act as a substrate, and blood cells and renal tubule epithelial cells are embedded therein. Casts as large as several tens of μm or more are present and owe their name to the fact that they are formed using a cylinder or the renal tubule lumen as a template. (Presence of casts suggests that there was a temporary occlusion with the renal tubule lumen, is considered important as findings indicating substantial renal disorder, and especially those enclosing blood cells or epithelial casts have significant clinical importance.)

Further, epithelial cells consist of squamous cells and transitional epithelium cells. Squamous cells have a circular or polygonal shape, are extremely thin and are created by detachment of a part of urinary tract. Meanwhile, transitional epithelium cells have diversified shapes such as a pear shape or a spinning top shape, and serve as component cells up to renal pelvis, urinary bladder and internal urethral opening. Their size ranges from those as small as several tens μm to those as large as 100 μm or more as represented by superficial cells.

Measurement of erythrocytes is important for judgment of presence or absence of hemorrhage in the route from kidney glomerulus to the urinary tract, and is frequently noticed with urine samples from patients with renal and urinary tract disorders, hemorrhagic disorders, leukemia or the like. Although erythrocytes are normally approximately 8 μm in size and are disk-like cells having a concave shape on both sides, in most cases, they present in the urine in a damaged form. In particular, erythrocytes derived from glomeruli are being deformed and are reduced in size. Erythrocytes with greater damage are hemolyzed and their contents are eluted.

Leukocytes are frequently found in urine samples from patients with renal infection, urinary tract infection, renal tuberculosis or the like. Therefore, it is possible to detect inflammation and infection at earlier stage through measurements of leukocytes in the urine sample. Leukocytes are from about 6 to 14 μm in size. Measurement of bacteria is an examination to check presence or absence of infection. The bacteria include cocci and bacilli. Cocci are spherical bacteria from about 0.5 to 2 μm in size, while bacilli are bacteria having a major axis in the range of about 2 to 10 μm. Cocci, if proliferated, result in a conglomeration of a chained shape representing an in-line moniliform or of a grape shape representing an irregularly and botryoidally-aggregated ones.

Conventionally, analysis of particles in urine has been performed by visual inspection using a microscope in a general laboratory. With this method, a urine sample is first subjected to centrifugal separation and enriched, sediments thus obtained are in some cases stained and then loaded on a microscope slide, and are subjected to classification and counting under the microscope. By the microscope inspection, first, presence or absence of urinary particles is checked and status of the urine sample is grasped under low-power field (LPF) (×100), and classification of each of constituents is performed under high-power field (HPF) (×400). Of measurement items, casts are small in number even if appeared. However, detection of this item is clinically highly useful and hence they are searched under low-power field (LPF). Other particles are classified under high-power field (HPF), erythrocytes and leukocytes are searched under high-power field (HPF) and their count is reported. As mentioned, urinary particle examination has three factors—qualitative examination (for example, "++" for bacteria), quantitative examination (for example, "5 cells/HPF" for erythrocytes) and morphological examination (for example, "presence of a poikilocyte is found" for erythrocytes).

For automation of urinary particle examination, an automatic microscope has been proposed. As a flow-type automatic microscope, UA-2000 (manufactured by Sysmex Corporation) is currently used. With this device, a urine sample is introduced to a flat type flow cell without concentration and images are taken and stored while it is flowing through the flow cell. The stored images are being sorted according to the size of particles, and a user observes the images and classifies them to each particle.

For such automatic microscope method, one designed to classify particles automatically has been proposed recently. However, urinary particles are diversified in their morphology and many particles are being damaged, and therefore, classification of images taken with good accuracy accompanies difficulties. It is particularly difficult to classify small-sized particles, such as erythrocytes (especially disrupted erythrocytes), bacteria and crystals with good accuracy, and user intervention is needed for re-classification.

As an automatic classification apparatus for urinary particle examination, a urinary particle measuring apparatus UF-100 based on the flow cytometer (manufactured by Sysmex Corporation) has been proposed. In this apparatus, urinary particles are stained by a stain reagent, and a scattered light signal and a fluorescence signal are combined to execute classification of erythrocytes, leukocytes, epithelial cells, casts and bacteria. As for a classification reagent, a dye for staining the membrane and nucleus of each particle is used, and morphology of urinary particles is maintained (see, for example, Japanese Patent Laid-Open No. 8-170960). As mentioned above, urinary particles are diversified in their morphology and many particles are being damaged, and it is difficult to execute classification with good accuracy only by a combination of scattered light signal intensity and fluorescence signal intensity of a flow cytometer. Hence, a configuration is proposed which utilizes a combination of intensity of the scattered light signal and its pulse width, intensity of the fluorescence signal and its pulse width to allow for classification of each of urinary particles (see, for example, U.S. Pat. No. 5,325,168). This urinary particle measuring apparatus based on the flow cytometer involves various ingenuities to allow for classification of urinary particles and presentation of morphology information. For example, information about origin of urinary erythrocytes (derived from glomeruli or from glomeruli) is presented through analysis of scattered light signals of erythrocytes (see, for example, U.S. Pat. No. 6,118,522). This apparatus enables automatic classification of urinary particles, thereby contributing greatly to automation of urine examinations.

Even if an apparatus designed to analyze scattered light signal and fluorescence signal by various methods is used, there are samples which hinder high-accuracy measurements. As a possible cause for this, it is mentioned that there are samples with which classification of bacteria is difficult. Bacteria, although considerably small in size, have diversified morphologies. For example, samples in which small-sized bacteria, namely spherical bacteria not in a conglomeration form, alone are dominant are mentioned. The apparatus mentioned above is composed so that large-sized particles (casts, epithelial cells), medium-sized particles (leucocytes, erythrocytes) and small-sized particles (bacteria) are measured at one time, which means measurements of large-sized particles of several tens μm are necessary, and therefore, detection of bacteria of 1 μm or smaller in their size with good accuracy was difficult. Bacteria measurement in the urinary particle examination is an examination to see whether or not bacteria appeared in an amount which could be confirmed by microscope inspection, and in general, presence or absence of bacteria about $10^4$ cells/ml or more is checked. If a bacteria concentration of $10^4$ cells/ml or more is available, cocci are proliferated and are mostly in a conglomeration form, which normally meets requirements of the urinary particle inspection. However, so far, samples with small-sized spherical bacteria not in a conglomeration form were occasionally overlooked.

On the other hand, samples with large-sized bacteria, namely, specimens in which spherical bacteria in a grown conglomeration or large-sized bacilli appeared, the range of bacteria appearance is widened and in some cases entered into the range of appearance of erythrocytes and leukocytes. Further, even if spreading into erythrocyte and leukocyte appearance range does not occur, their appearance range overlaps with that of mucus fibril, yeast-like fungi and sperms, thereby inviting, in some cases, erroneous results in the bacteria measurement.

In the meantime, although depending on the clinical purpose intended, a high-sensitivity examination is also required for the bacteria test of urine. However, detection of fewer numbers of bacteria by visual examination under a microscope is difficult particularly for small-sized bacteria, and this is not used for examinations which need high-sensitivity. In this case, a cultivation test in which a specimen is cultured to be subjected to the examination is carried out in the bacteria laboratory separately from urinary particle inspection. Since cultivation test needs considerable number of days for cultivation, it is proposed that high-sensitivity bacteria test be performed without cultivation.

Bacteria analysis utilizing flow cytometry, namely, a method in which bacteria are stained by a stain reagent and are measured by a scattered light signal and a fluorescence signal, has been proposed. For example, European Patent Application Publication No. EP1136563 and U.S. Patent Application Publication No. U.S. 2002/0076743 disclose a method for measuring specimens such as urine containing foreign substances having a similar size as that of bacteria with good accuracy with the use of a dying reagent containing a cationic surfactant to allow for dissolution of foreign substances other than bacteria.

SUMMARY

The scope of the present invention is defined solely by the appended claims, and is not affected to any degree by the statements within this summary. A first apparatus, intended for use in analyzing particles in urine, embodying features of the present invention comprises: a specimen preparing section for preparing one or more specimens by using a urine sample, a first stain reagent and a second stain reagent; an optical detecting section comprising a light source for irradiating the one or more specimens with light, a scattered light receiving element for detecting light scattered from the one or more specimens, and a fluorescence receiving element for detecting fluorescence emitted from the one or more specimens; a first measurement section for measuring particles in urine containing at least erythrocytes, based on scattered light and fluorescence detected by the optical detecting section; and a second measurement section for measuring bacteria in urine, based on scattered light and fluorescence detected by the optical detecting section.

A second apparatus, intended for use in analyzing particles in urine, for measuring bacteria contained in urine and urinary particles containing at least erythrocytes embodying features of the present invention comprises: a sample distribution section for distributing urine samples to a first aliquot and a second aliquot; a first specimen preparing section for preparing a first specimen for measuring urinary particles, containing at least erythrocytes, by mixing a first stain reagent and the first aliquot; a second specimen preparing section for preparing a second specimen for measuring bacteria by mixing a second stain reagent and the second aliquot; an optical detecting section comprising a light source for irradiating a light to a specimen being supplied, a scattered light receiving element for detecting scattered light emitted from the specimen, and a fluorescence receiving element for detecting fluorescence emitted from the specimen; and a temperature regulating section for regulating a temperature of the first specimen preparing section to a first temperature and regulating a temperature of the second specimen preparing section to a second temperature higher than the first temperature.

A first method, intended for use in analyzing particles in urine, embodying features of the present invention comprises: a) preparing one or more specimens by using a urine sample, a first stain reagent and a second stain reagent; b) irradiating light to the one or more specimens, and detecting scattered light and fluorescence emitted from the one or more specimens; c) measuring particles in urine containing at least erythrocytes, based on scattered light and fluorescence detected from one of the one or more specimens; and d) measuring bacteria in urine, based on scattered light and fluorescence detected from one of the one or more specimens.

A second method, intended for use in analyzing particles in urine, for measuring bacteria contained in urine and urinary particles containing at least erythrocytes, embodying features of the present invention comprises: a) distributing a urine sample to a first aliquot and a second aliquot; b) preparing a first specimen for measurement of urinary particles containing at least erythrocytes, by mixing a first stain reagent and the first aliquot; c) preparing a second specimen for measurement of bacteria by mixing a second stain reagent and the second aliquot; d) detecting scattered light and fluorescence emitted from the first specimen by irradiating light to the first specimen; and e) detecting scattered light and fluorescence emitted from the second specimen by irradiating light to the second specimen.

DETAILED DESCRIPTION OF THE PREFERRED EMBODIMENTS

Figure 1:
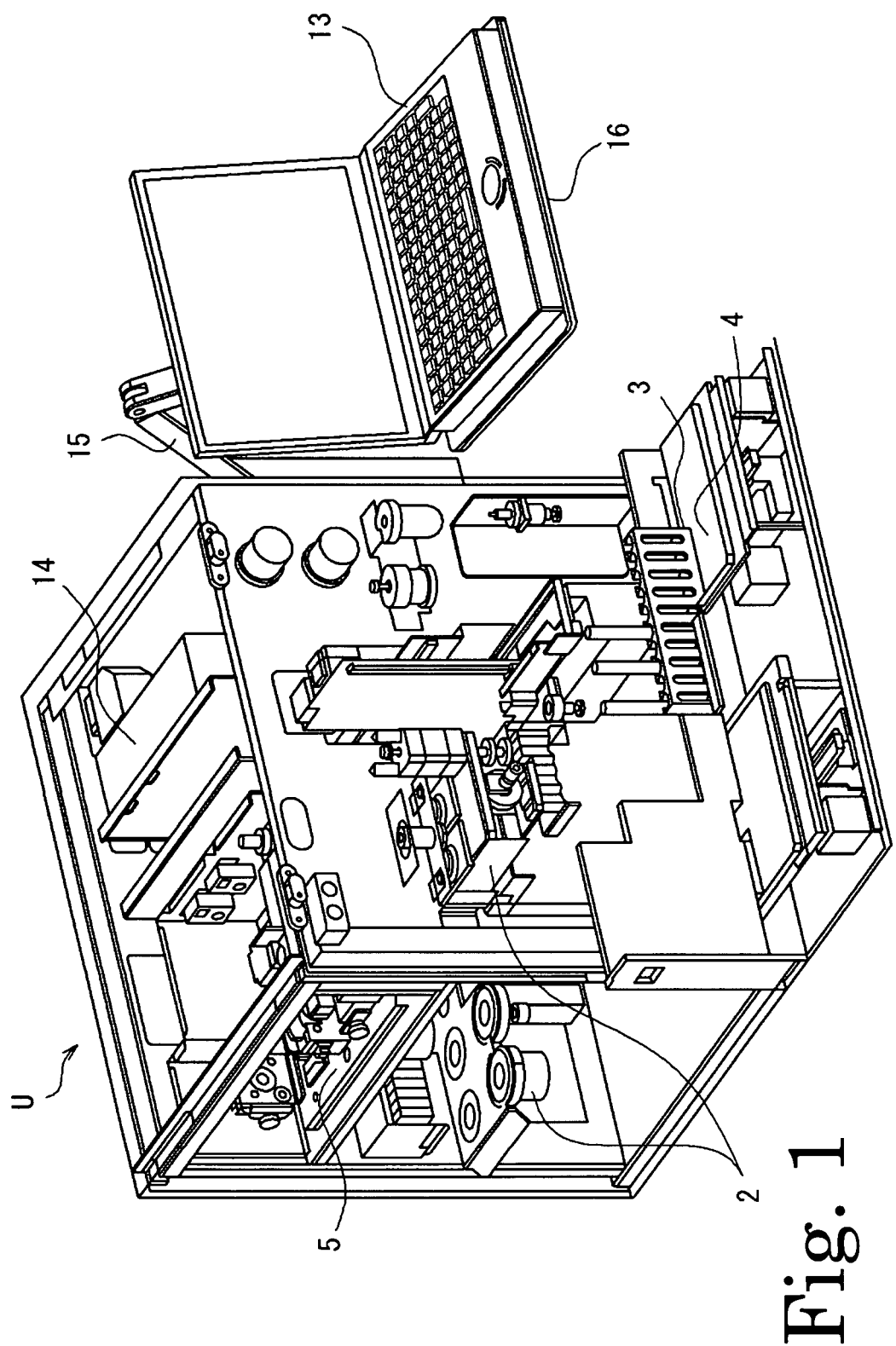
FIG. 1 is a perspective view explaining one embodiment of an apparatus for analyzing particles in urine according to the present invention.

Referring now to the attached drawings, embodiments of the apparatus for analyzing particles in urine relating to one embodiment according to the present invention will be explained in detail. FIG. 1 is a perspective view explaining a main unit of the apparatus for analyzing particles in urine relating to one embodiment according to the present invention and a personal computer attached thereto. In FIG. 1, a chassis for accommodating components of the apparatus for analyzing particles in urine is omitted in part to facilitate good understanding.

Composition of Apparatus

In FIG. 1, an apparatus for analyzing particles in urine (main unit) U includes a specimen preparing section 2 for preparing a specimen, a rack table 4 for transferring a sample rack (test tube stand) 3, an optical detecting section 5 for detecting information about urinary particles and bacteria from the specimen, and a circuit section 14. A support stand 16 is provided to the chassis side face via an arm 15, and a personal computer 13 is mounted thereon. The personal computer 13 is connected to the circuit section 14 of the apparatus for analyzing particles in urine U via LAN connection.

Figure 2:
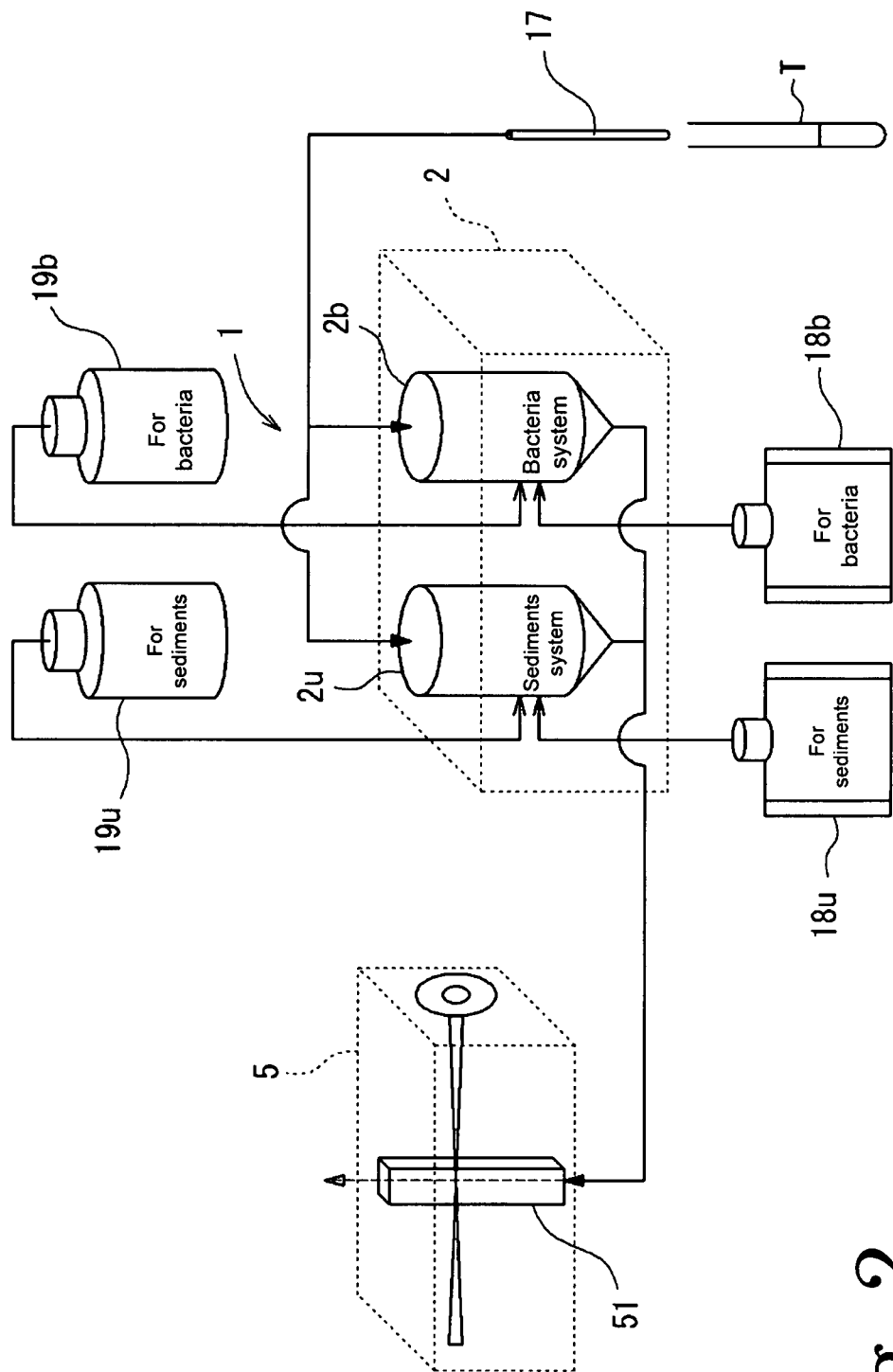
FIG. 2 is a drawing showing an outline of a functional composition of a specimen preparing section and an optical detecting section of the apparatus for analyzing particles in urine.

FIG. 2 is a drawing showing an outline of a functional composition of the specimen preparing section 2 and the optical detecting section 5. In FIG. 2, urine (sample) contained in a test tube T is sucked by a syringe pump (not shown) using a suction pipe 17 and is dispensed to the specimen preparing section by a sample distribution section 1. The specimen preparing section in the present embodiment is composed of a specimen preparing section (first specimen preparing section) 2u and a specimen preparing section (second specimen preparing section) 2b, the sample distribution section 1 distributes aliquots of quantified urine (sample) to each of the specimen preparing section 2u and the specimen preparing section 2b.

To the urine aliquots in the specimen preparing section 2u are mixed with a dilute solution 19u and a dyeing solution (stain reagent) 18u, and dyeing is performed by dyes contained in the dyeing solution (stain reagent) 18u. This stained specimen is used as a suspending solution for analyzing relatively large urinary particles (urinary sediments) such as erythrocytes, leukocytes, epithelial cells and casts. Meanwhile, to the urine aliquots in the specimen preparing section 2b are mixed a dilute solution 19b and a dyeing solution (stain reagent) 18b, and dyeing is performed by dyes contained in the dyeing solution (stain reagent) 18b. This stained specimen is used as a suspending solution for analyzing bacteria.

With regard to two types of suspending solutions (specimens) prepared as mentioned above, the suspending solution (first specimen) of the specimen preparing section 2u is first introduced to the optical detecting section 5, forms a fine stream being wrapped by a sheath solution in a sheath flow cell 51, and laser light is irradiated thereto. Following this, in a similar fashion, the suspending solution (second specimen) of the specimen preparing section 2b is introduced to the optical detecting section 5, forms a fine stream in the sheath flow cell 51, and laser light is irradiated thereto. These operations are carried out automatically by actuating driving units and solenoid valves (not shown) by controlling a microcomputer 11 (control apparatus), which will be described later.

Figure 3:
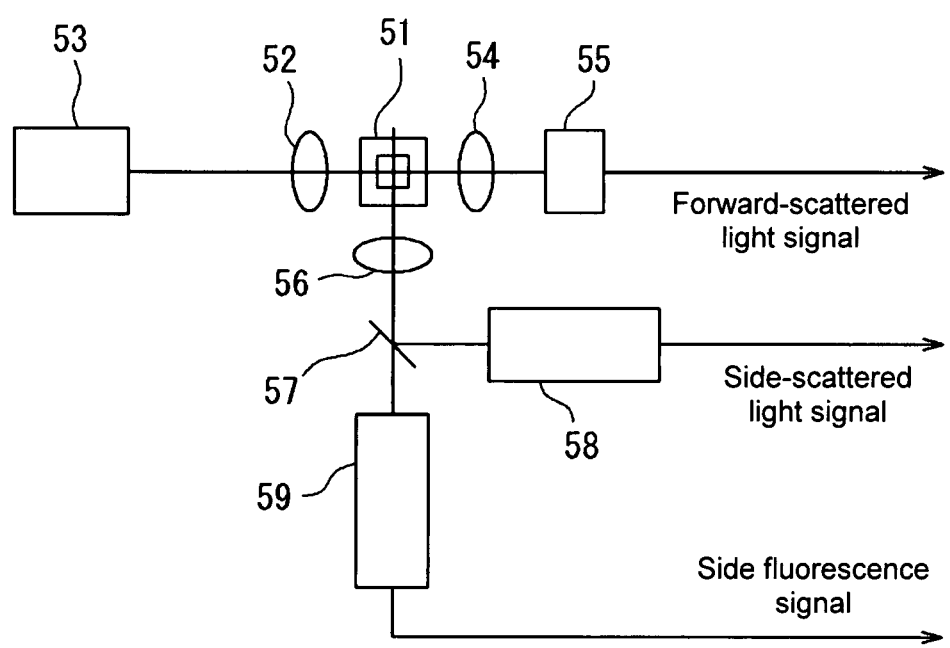
FIG. 3 is a drawing showing a composition of the optical detecting section.

FIG. 3 is a drawing showing a composition of the optical detecting section 5. In FIG. 3, a condenser lens 52 focuses laser light irradiated from a semiconductor laser 53, which acts as the light source, onto the sheath flow cell 51, and a collecting lens 54 focuses forward-scattered light of urinary particles onto a photodiode 55, which acts as a scattered light receiving element. Further, another collecting lens 56 focuses side scattered light and side fluorescence of the particles onto a dichroic mirror 57. The dichroic mirror 57 reflects side scattered light on a photomultiplier 58, which acts as a scattered light receiving element and causes side fluorescence to be transmitted towards a photomultiplier 59, which acts as a fluorescence receiving element. These optical signals are considered to reflect features of urinary particles. The photodiode 55, photomultiplier 58 and photomultiplier 59 convert optical signals to electrical signals, and each outputs a forward scattered light signal (FSC), a side scattered light signal (SSC), and a side fluorescence signal (SFL), respectively. After being amplified by a preamplifier (not shown), these outputs are subjected to the next processing.

As for the light source, although a gas laser may be used in lieu of the semiconductor laser, it is preferable to employ a semiconductor laser from the viewpoints of low costs, small-size and low power consumption, and employment of a semiconductor laser could reduce product costs and at the same time, allow realization of small-sized apparatus and electrical power saving. Further, among semiconductors lasers, a red semiconductor laser is preferably used due to low costs, long service life and stable supply by the manufacturers.

Figure 6:
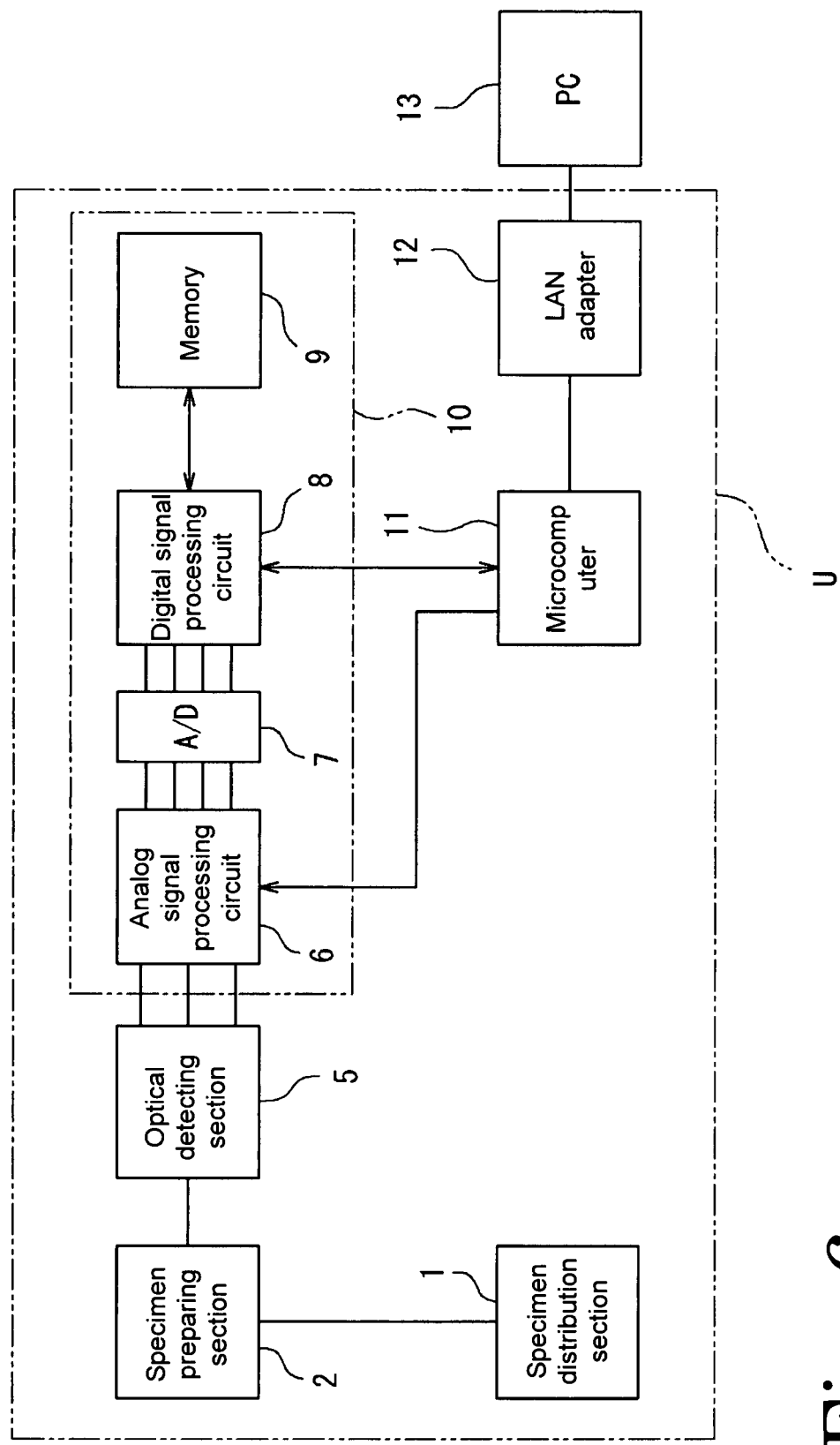
FIG. 6 is a block diagram showing a whole composition of the apparatus for analyzing particles in urine shown in FIG. 1.

FIG. 6 is a block diagram showing a whole composition of the apparatus for analyzing particles in urine U. In FIG. 6, the apparatus for analyzing particles in urine U includes the above-mentioned sample distribution section 1, specimen preparing section 2, and optical detecting section 5, an analog signal processing circuit 6 for executing amplification and filter processing of the output of the optical detecting section 5 for those being amplified by the preamplifier, an A/D converter 7 for converting the output of the analog signal processing circuit 6 to a digital signal, a digital signal processing circuit 8 for executing a predetermined waveform processing for digital signals, memory 9 connected to the digital signal processing circuit 8, the microcomputer 11 connected to the analog signal processing circuit 6 and the digital signal processing circuit 8, and a LAN adapter 12 connected to the microcomputer 11. The personal computer 13 (analysis section) provided outside is LAN connected to the apparatus for analyzing particles in urine U via this LAN adapter 12, and analysis of data acquired by the apparatus for analyzing particles in urine U is carried out by the personal computer 13. The analog signal processing circuit 6, A/D converter 7, digital signal processing circuit 8, and memory 9 compose a signal processing circuit 10 for electric signals being output by the optical detecting section 5.

Urinary Particle Measuring Reagent

As for reagents for measuring urinary particles, Japanese Patent Laid-Open No. 8-170960 provides detailed description. In one embodiment of the reagents, a dye for membrane staining is selected in order to stain even particles without nuclei. As for a reagent, an osmotic pressure compensation agent is added for the sake of prevention of erythrocyte hemolysis and acquirement of stable fluorescence intensity, and it is adjusted to 100 to 600 mOsm/kg in order to obtain osmotic pressure suited for classification and measurement. Cell membranes and nuclei (nuclear membrane) of urinary particles are stained by this reagent. As for a stain reagent containing a dye for membrane staining, a condensed benzene derivative is used and, for example, NK-529 (trade name, manufactured by Hayashibara Biochemical Labs.) that is a cyanine dye may be used. Meanwhile, this stain reagent is designed to stain nuclear membrane as well as cell membranes. When such a stain reagent is used, for nucleated cells such as leukocytes and epithelial cells, dyeing intensity in the cellular cytoplasm (cell membrane) and the same in nucleus (nuclear membrane) are joined together, and this allows for discrimination of nucleated cells such as leukocytes and epithelial cells from urinary particles without nucleus such as erythrocytes or the like.

Bacteria Analysis Reagent

As for reagents for measuring bacteria with good accuracy also for specimens such as urine containing similar size foreign substances, European Patent Application Publication No. EP1136563 provides detailed description. In one embodiment of the reagents, a dye for nucleic acid staining is used. As for stain reagents containing a dye for nucleus staining, for example, a cyanine dye represented by the following chemical structure (1) and disclosed by U.S. Patent Application Publication No. U.S. 2002/0076743 may be used.

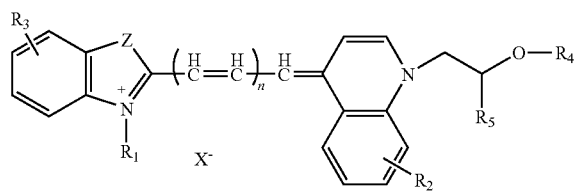

(1)

Of these, a cyanine system dye represented by the following chemical structure (2) may be used preferably.

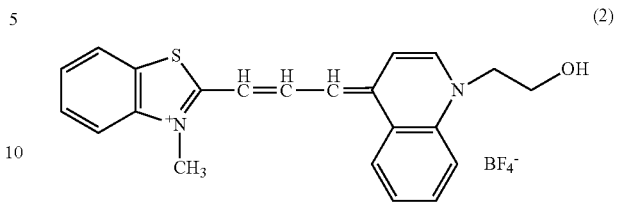

(2)

In this case, it is preferable that a stain reagent (first stain reagent) to be added to a urine sample for measurement of urinary particles containing at least erythrocytes contains a dye for membrane staining, while a stain reagent (second stain reagent) to be added to the urine sample for measurement of bacteria contains a dye for nucleic acid staining. Since urinary particles contain those having no nucleus such as erythrocytes, it is possible to detect urinary particles including those having no nucleus when the first stain reagent contains a dye for membrane staining. Further, when the second stain reagent contains a dye for-nucleus staining, nuclei of bacteria are stained effectively, and it is possible to make a measurement of the bacteria with good accuracy even if they are small in size.

Figure 4:
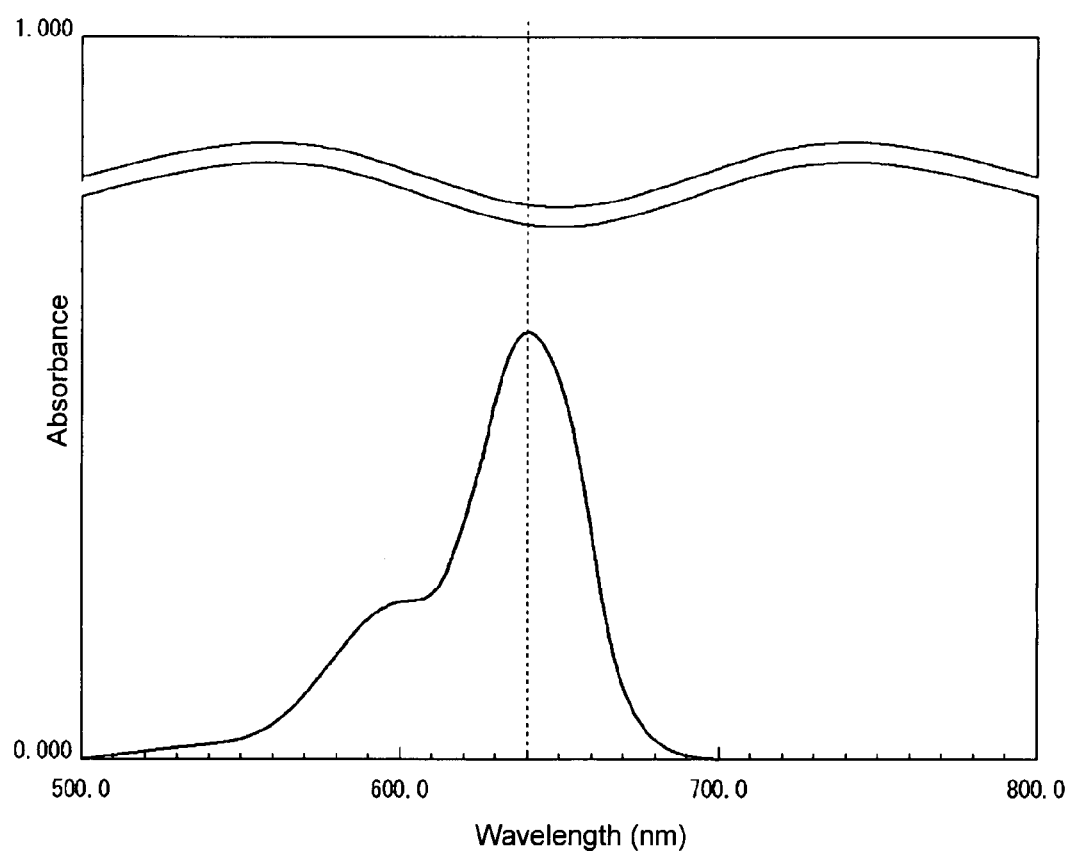
FIG. 4 is a drawing showing a relationship between absorption wavelength and absorbance of one example of a first stain reagent.
Figure 5:
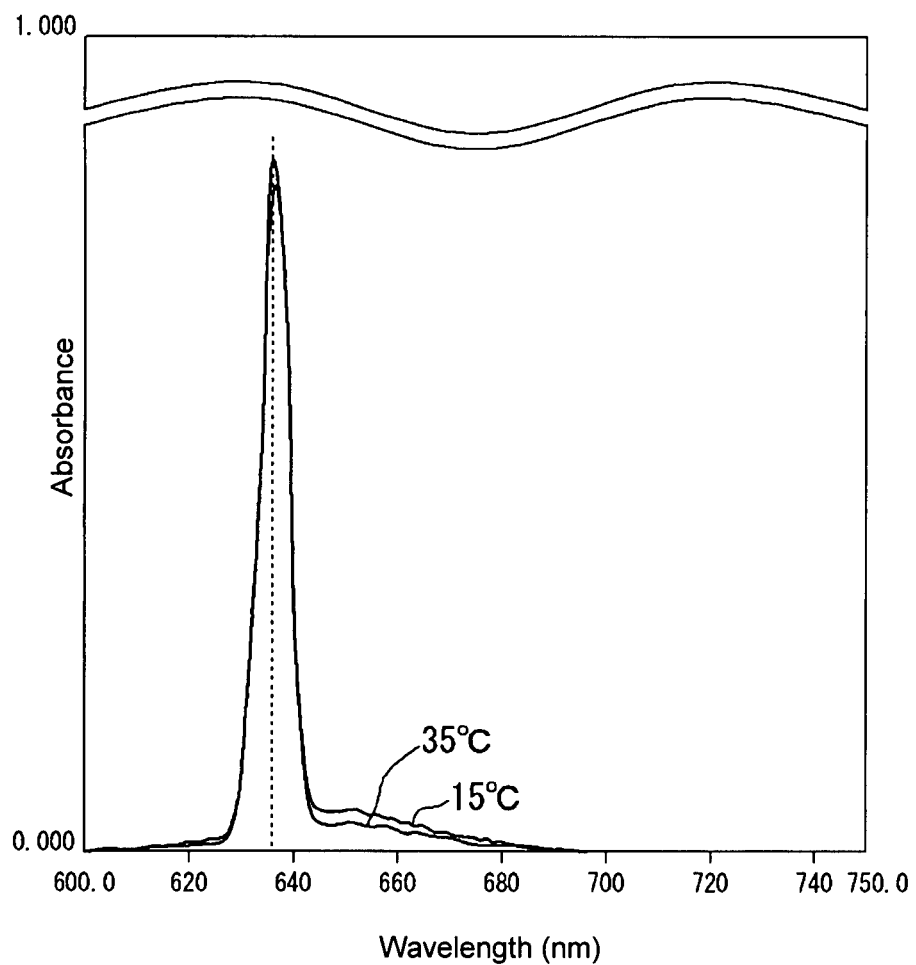
FIG. 5 is a drawing showing a relationship between absorption wavelength and absorbance of one example of a second stain reagent.

Further, it is preferable that, for the first stain reagent and the second stain reagent, a peak of absorption wavelength is present in proximity to luminescence wavelength of the semiconductor laser. By selecting the peak of absorption wavelength of the first stain reagent and the second stain reagent so that it may present in proximity to the luminescence wavelength of the semiconductor laser, it becomes possible to make a measurement of stained urinary particles and bacteria by the semiconductor laser. FIG. 4 is a drawing showing a relationship between absorption wavelength and absorbance of one example of the first stain reagent of this sort (stain reagent containing NK-529 (trade name, manufactured by Hayashibara Biochemical Labs.)), in which a peak of absorption wavelength exists at 640 nm in the vicinity of the luminescence wavelength (635 nm) of a red semiconductor laser. FIG. 5 is a drawing showing a relationship between absorption wavelength and absorbance of one example of the second stain reagent (stain reagent containing a cyanine dye represented by the chemical structure (2) and disclosed in U.S. Patent Application Publication No. U.S. 2002/0076743), in which a peak of absorption wavelength exists at 636 nm in the vicinity of the luminescence wavelength (635 nm) of a red semiconductor laser. Although FIG. 5 shows changes in absorbance for cases where reagent temperatures are 15° C. and 35° C., it is noticed from this that there is no big change in absorbance of reagents insofar as the temperature is around room temperature.

For bacteria measurement reagents, a cationic surfactant is included in order that dyes pass through a membrane thereby promoting quick staining and for the sake of shrinkage of foreign substances such as mucus fibril and debris of erythrocytes. In this case, since it is possible to give damage to cell membranes of bacteria by the surfactant, nucleic acid of bacteria can be stained effectively by the dye contained in the second stain reagent. As a result, measurement of the bacteria can be performed with further improved accuracy after a dyeing processing in a short period of time. Meanwhile, in a case where a surfactant is mixed to the second aliquot, it is preferably configured so that measurement of bacteria takes place upon completion of measurement of urinary particles. Since the surfactant is contained in the second specimen, if measurement of urinary particles is made after bacteria measurement, the surfactant is mixed into the first specimen due to carry-over of the specimen, membrane of the urinary particles containing erythrocytes is damaged, and there is a possibility that measurements of the urinary particles are eventually affected. However, if it is configured so that measurement of bacteria is made after completion of measurement of urinary particles, mixing of the surfactant into the first specimen can be prevented and measurement of urinary particles can be done with good accuracy.

According to the present embodiment, the first specimen for measurement of urinary particles containing at least erythrocytes and the second specimen for measurement of bacteria are prepared from one urine sample, respectively, and urinary particles containing at least erythrocytes are measured by the first specimen and bacteria are measured by the second specimen. With this configuration, one analysis apparatus is able to make a measurement of urinary particles containing at least erythrocytes and bacteria with high accuracy, respectively. In addition, since the optical detecting section is commonly used by the first specimen and the second specimen, composition of the apparatus can be simplified, thereby reducing products costs and downsizing the apparatus.

Figure 7:
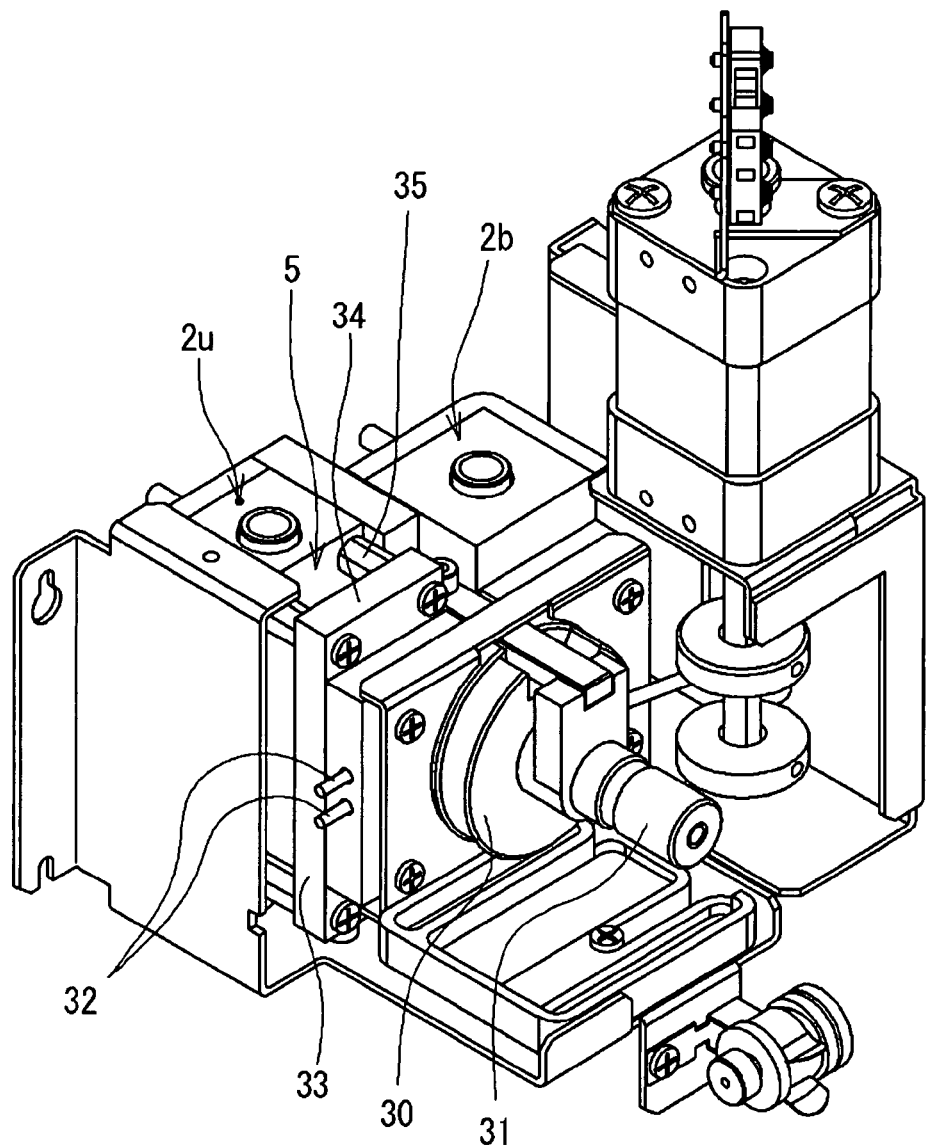
FIG. 7 is a diagrammatic perspective view of a quantifying mechanism and the specimen preparing sections of the apparatus for analyzing particles in urine.
Figure 8:
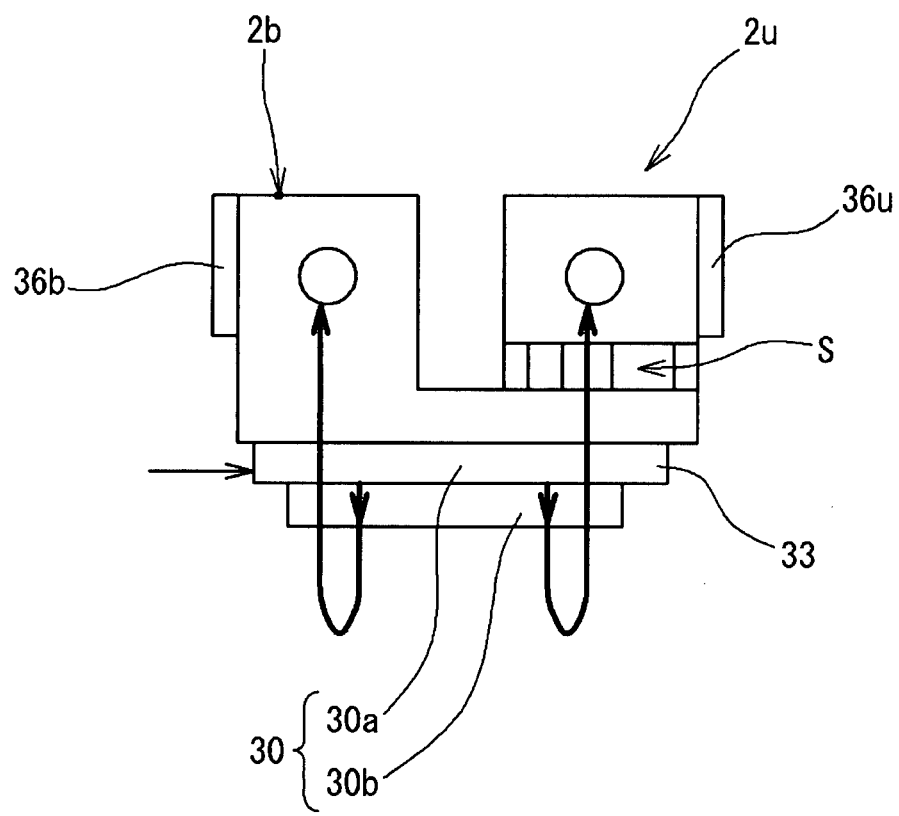
FIG. 8 is a drawing explaining the quantifying mechanism and the specimen preparing section of the apparatus for analyzing particles in urine.

FIG. 7 is a diagrammatic perspective view of the quantifying mechanism and the specimen preparing sections of the apparatus for analyzing particles in urine relating to the present embodiment, and FIG. 8 is a drawing explaining them. According to the present embodiment, a sampling valve 30, which is used regularly, is employed as the quantifying mechanism for distributing a predetermined amount of urine sample to the specimen preparing section (first specimen preparing section) 2u and the specimen preparing section (second specimen preparing section) 2b. This sampling valve 30 includes two disk-like fixed elements and a movable element being sandwiched by the fixed elements, and the movable element is turned by a motor 31.

The sampling valve 30 is equipped with two discs 30a, 30b made of alumina ceramics superimposed with each other. A flow path is formed inside of the disks 30a, 30b for circulation of the sample, the flow path is isolated when one disk 30b is turned around the center axis thereof, thereby quantifying the sample. Such sampling valve 30 is composed so as to form one unit with the specimen preparing section 2b via a hydraulic cassette 33 having a flow path 32 for the specimen inside. In other words, the sampling valve 30, the hydraulic cassette 33, and the specimen preparing section 2b are disposed so as to thermally form one unit being in close contact with each other, and are configured so that the temperature of the sampling valve 30 may become almost identical with that of the specimen preparing section 2b. In the meantime, the specimen preparing section 2u is fixed by a bolt 35 to a mounting plate 34 fixed to the chassis while a predetermined clearance S is provided, and therefore, the specimen preparing section 2u is being almost thermally isolated from the sampling valve 30 and the specimen preparing section 2b.

The specimen preparing section 2u and the specimen preparing section 2b are heated by heaters 36u, 36b, respectively, each composing a temperature regulating section. With this configuration, the temperature of the specimen preparing section 2u for preparing the first specimen is regulated to a first temperature and at the same time, the temperature of the specimen preparing section 2b for preparing the second specimen is regulated to a second temperature higher than the first temperature. In particular, the specimen preparing section 2u is regulated to attain approximately 35±2° C. and the specimen preparing section 2b is regulated to attain approximately 42±2° C., that is higher than the former. The higher the temperature of a specimen being set, the faster the prescribed portion (membrane or nucleus) of erythrocytes or bacteria contained in the specimen is stained, thereby shortening the time for measurements. On the other hand, erythrocytes are easily damaged at high-temperatures, and if the temperature is set too high, correct measurement is not possible. Hence, it is possible to make measurements of urinary particles containing erythrocytes together with bacteria with good accuracy if the temperature of the second specimen for measuring bacteria with higher heat resistance compared to other urinary particles is regulated to be higher than the temperature of the first specimen for measuring urinary particles; in other words, the specimen preparing section 2u and the specimen preparing section 2b are regulated to a temperature suitable for the measurement, respectively. Meanwhile, the temperature of the specimen preparing section 2u and the specimen preparing section 2b may be measured by, for example, a thermistor. It is then possible to regulate the specimen preparing section 2u and the specimen preparing section 2b to the prescribed range of the temperature, respectively, by ON-OFF control of the heaters 36u, 36b based on the results of measurements thus obtained.

Further, if the sampling valve 30 and the specimen preparing section 2b are composed to thermally form one unit, it is possible to prevent cooling of a specimen, which has been temperature-regulated by the sampling valve 30, when being supplied to the specimen preparing section 2b. This can reduce losses related to the temperature regulation. In this case, for a specimen being supplied to the specimen preparing section 2u which is kept at a lower temperature than the specimen preparing section 2b, its temperature could be reduced naturally while being supplied from the sampling valve 30, if so configured that the flow path of the specimen passes through the clearance S.

Analysis Procedures

Figure 9:
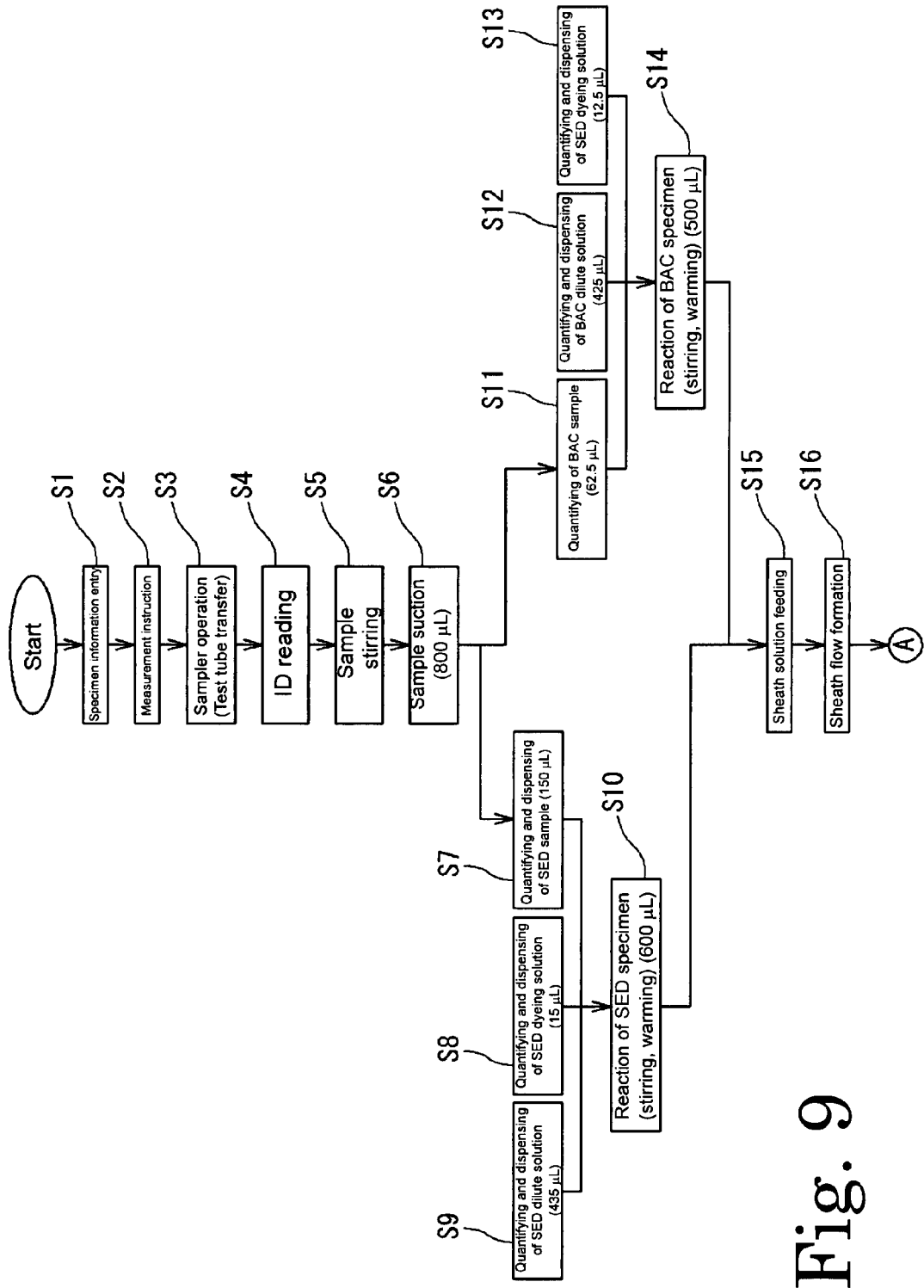
FIG. 9 is a flowchart (first half) showing urine analysis procedures using the apparatus for analyzing particles in urine relating to one embodiment according to the present invention.
Figure 10:
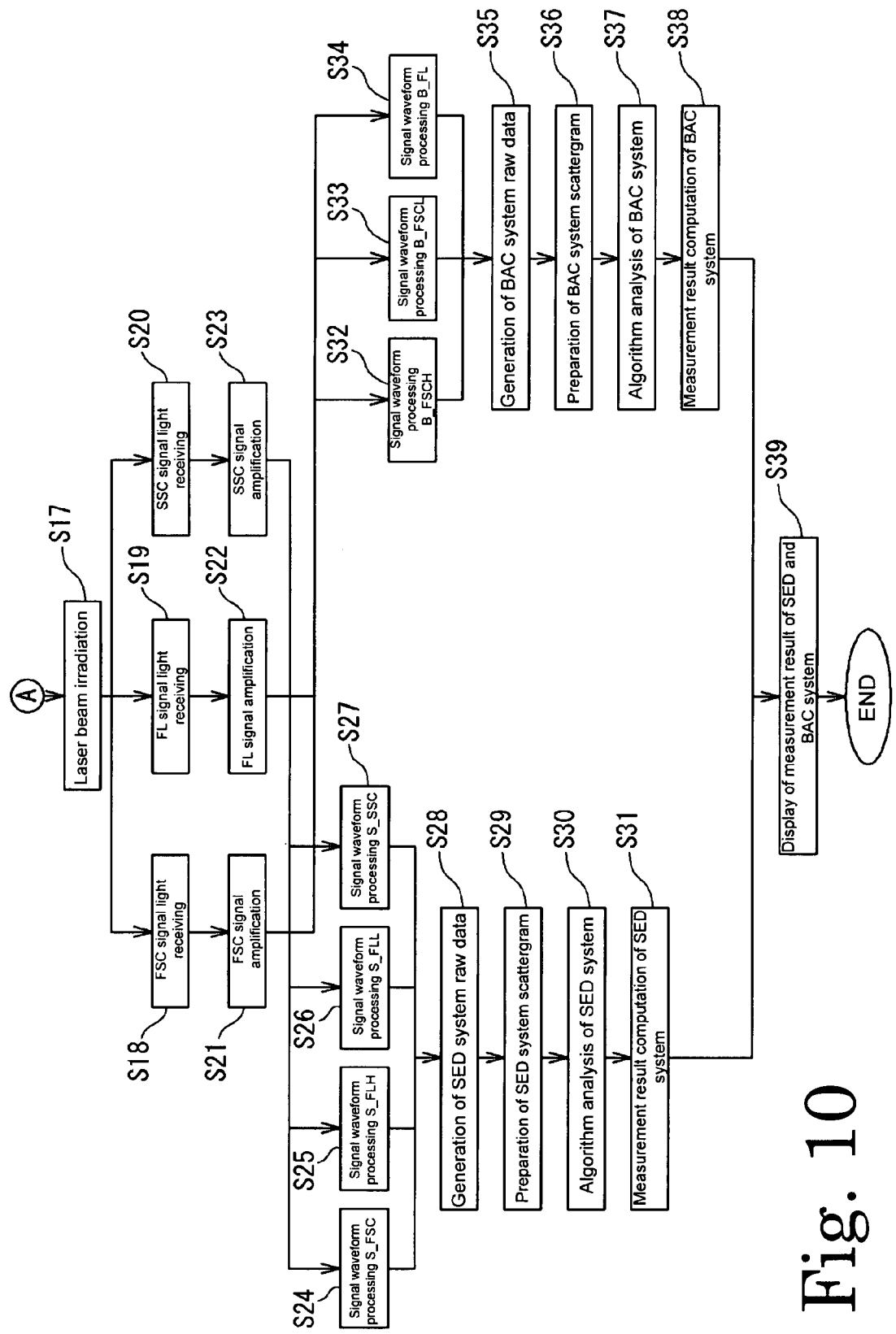
FIG. 10 is a flowchart (second half) showing urine analysis procedures using the apparatus for analyzing particles in urine relating to one embodiment according to the present invention.

Next, referring to flow charts shown in FIG. 9 to FIG. 10, urine analysis procedures using the apparatus for analyzing particles in urine related to one embodiment according to the present invention will be explained.

First, specimen information such as sample number, patient information such as name, age, gender, clinical specialty associated with the sample number, and measurement items being controlled by a host computer are obtained from the host computer (Step S1). A measurement execution instruction is then given by input means such as a keyboard or a mouse of the personal computer 13 (Step S2). Upon receiving this instruction, the sample rack 3 in which are set test tubes T each containing the sample is transferred by the rack table 4 to a predetermined suction position (Step S3). The test tube T is turned at this suction position and a barcode printed on an ID label, which is pasted on the outer circumference of the test tube T, is being read (Step S4). The sample number of the sample is then known, which is then verified with the sample information acquired in step S1, and measurement items of the sample can be identified.

Then, the suction pipe 17 goes down, a front edge of the suction pipe 17 is inserted into the sample in the test tube T, and the sample is lightly sucked and discharged repeatedly in this state so that the sample may be stirred (Step S5). After being stirred, a predetermined amount (800 µL) of the sample is sucked, 150 µL and 62.5 µL of the sample is each dispensed by the sampling valve 30 to the specimen preparing section 2u for preparing a specimen for the measurement of urinary particles containing at least erythrocytes (SED) and to the specimen preparing section 2b for preparing a specimen for the measurement of bacteria (BAC) contained in the urine, respectively (Step S7 and Step S11).

To the specimen preparing section 2u are quantified and dispensed a predetermined amount of a dyeing solution (stain reagent) and a dilute solution together with the sample (Step S8 and Step S9). Similarly, to the specimen preparing section 2b are quantified and dispensed a predetermined amount of a dyeing solution (stain reagent) and a dilute solution together with the sample (Step S12 and Step S13). The specimen preparing section 2u and the specimen preparing section 2b are being heated by the heaters 36u, 36b to a predetermined temperature, respectively, and stirring of the specimen is carried out by a propeller type stirrer (not shown) (Step S10 and Step S14). Meanwhile, the dilute solution dispensed to the specimen preparing section 2u in Step S9 includes a surfactant, which gives damage to cell membranes, thereby allowing efficient dyeing of nuclei of bacteria.

Following this, a sheath solution is sent to the sheath flow cell 51 of the optical detecting section 5 (Step S15), the specimen for the measurement of urinary particles (SED) is then introduced to the optical detecting section 5, and a fine stream (sheath flow) wrapped by the sheath solution is formed in the sheath flow cell 51 (Step S16). Laser beam from the semiconductor laser 53 is irradiated to the sheath flow thus formed (Step S17). The reason why the measurement of urinary particles is performed first is that since a bacteria measurement specimen includes a surfactant, if urinary particle measurement is performed after bacteria measurement, the surfactant is mixed into the specimen for urinary particle measurement due to carry-over of the specimen, membrane of the urinary particles containing erythrocytes is damaged, thereby affecting the measurement of the urinary particles in some cases.

Forward-scattered light, fluorescence, and side-scattered light of urinary particles generated by the laser beam irradiation are received by the photodiode 55, photomultiplier 59, and photomultiplier 58, respectively, converted to electric signals, and are output as a forward-scattered light signal (FSC), a fluorescence signal (FL), and a side-scattered light signal (SSC) (Steps S18 to 20). These outputs are amplified by the preamplifier (Steps S21 to 23).

Upon completion of measurement by the specimen for measuring urinary particles (SED), bacteria in the urine are measured subsequently using the specimen prepared in Step S14. In this case, in a similar fashion as observed in Steps S15 to 23, a forward-scattered light signal (FSC) and a fluorescence signal (FL) are output by the optical detecting section 5 used in the measurement of urinary particles, and amplified.

The forward-scattered light signal (FSC), fluorescence signal (FL), and side-scattered light signal (SSC) thus amplified are converted to digital signals in the signal processing circuit 10 (see FIG. 6) and at the same time, subjected to the predetermined waveform processing (Steps S24 to 27), and are transmitted to the personal computer 13 via the LAN adapter 12. In the meantime, "FLH" in Step S25 is high-sensitivity one obtained by amplifying the fluorescence signal (FL) with higher gain, and "FLL" in Step S26 is low-sensitivity one obtained similarly by amplifying the fluorescence signal (FL) with lower gain.

Then, raw data of the urinary particles (SED) are generated in the personal computer 13 (Step S28) and at the same time, a scattergram is generated based on the data (Step S29). Then, clustering of the scattergram prepared by algorithm analysis is performed (Step S30), and the number of particles is counted for every cluster (Step S31).

For bacteria, in a similar fashion, the forward-scattered light signal (FSC) and the fluorescence signal (FL) being amplified are converted to digital signals in the signal processing circuit 10 and at the same time, subjected to the predetermined waveform processing (Steps S32 to 34). In the meantime, "FSCH" in Step S32 is high-sensitivity one obtained by amplifying the forward-scattered light signal (FSC) with higher gain, and "FSCL" in Step S33 is low-sensitivity one obtained similarly by amplifying the forward-scattered light signal (FSC) with lower gain.

Then, they are transmitted to the personal computer 13 via the LAN adapter 12. Raw data of the bacteria (BAC) are generated in the personal computer 13 (Step S35), and a scattergram is generated based on the data (Step S36). Then, clustering of the scattergram prepared as mentioned by algorithm analysis is performed (Step S37), and the number of particles is counted for every cluster (Step S38). Results of the measurement obtained as mentioned above are displayed on a display which is a display means of the personal computer 13 (Step S39).

As measurement results of the urinary particles (SED), scattergrams are generated from each of signals of forward-scattered light, side-scattered light, and fluorescence. FIG. 11(a) is a scattergram in which the horizontal axis represents fluorescence intensity (low-sensitivity) (FLL) and the vertical axis represents forward-scattered light intensity (FSC). Epithelial cells (EC) and leukocytes (WBC), which are large cells having nuclei, appear in a region of strong fluorescence signal intensity. Majority of epithelial cells are larger in cell size than leukocytes and appear in a region where fluorescence intensity is stronger than that of leukocytes, while the range of appearance of some small-sized epithelial cells overlaps with that of leukocytes. In order to distinguish the both, a side-scattered light signal is used. FIG. 11(b) is a scattergram in which the horizontal axis represents side-scattered light intensity (SSC) and the vertical axis represents forward-scattered light intensity (FSC). Since epithelial cells appear in a region where side-scattered light intensity is stronger than leukocytes, epithelial cells are identified from this scattergram.

FIG. 11(c) is a scattergram in which the horizontal axis represents fluorescence intensity (high-sensitivity) (FLH) and the vertical axis represents forward-scattered light intensity (FSC) and shows a region where fluorescence intensity is low. Erythrocytes (RBC) have no nuclei and therefore are found in regions where fluorescence intensity is low. Some crystals (X'TAL) appear in regions of erythrocytes appearance, and therefore, a side-scattered light signal is used for confirmation of appearance of crystals. FIG. 11(b) is a scattergram in which the horizontal axis represents side-scattered light intensity (SSC) and the vertical axis represents forward-scattered light intensity (FSC). With crystals, the center of distribution of side-scattered light intensity is not constant, crystals appear in regions where the intensity is high, and therefore, discrimination from erythrocytes is performed from this scattergram.

FIG. 11(d) is a scattergram in which the horizontal axis represents fluorescence width (FLLW) and the vertical axis represents fluorescence width 2 (FLLW2). FLLW indicates a width of a fluorescence signal to capture particles in which cell membranes are stained and FLLW2 indicates a width of a stronger fluorescence signal such as nuclei. As shown in the drawing, FLLW of casts (CAST) is greater and FLLW2 of casts with contents (P. CAST) is greater. Further, casts without contents (CAST) appear in regions where FLLW2 is low. Here, a width of a signal reflects length of time during which an optical signal is being detected on a pulse-like signal waveform where the vertical axis represents signal intensity and the horizontal axis represents time.

Figure 11:
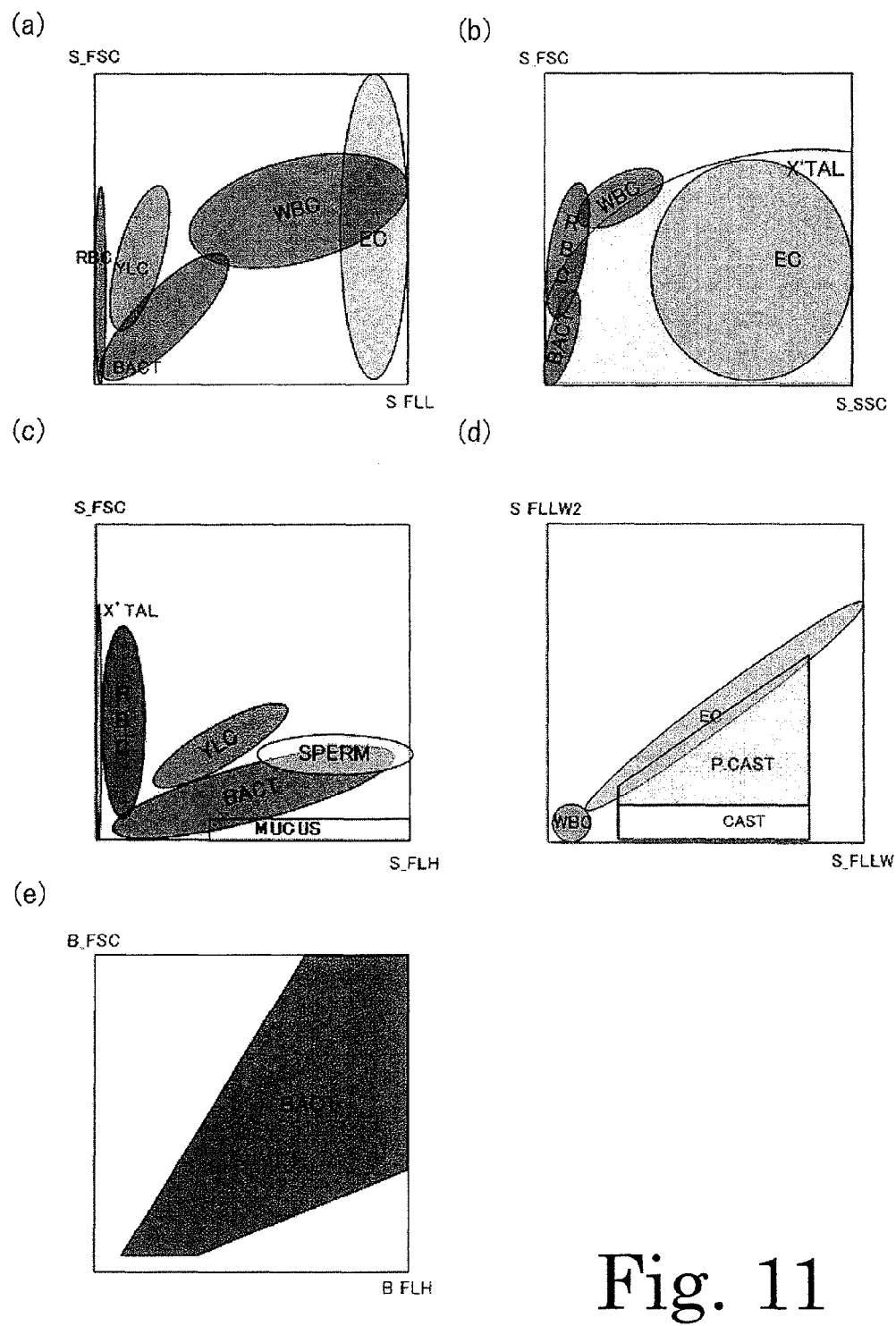
FIGS. 11(a) to 11(e) are drawings showing one example of a scattergram obtained by the apparatus for analyzing particles in urine relating to one embodiment according to the present invention.

With another result of measurements of bacteria, scattergrams are generated from forward-scattered light signal and fluorescence signal. FIG. 11(*e*) is a scattergram in which the horizontal axis represents fluorescence intensity (B-FLH) and the vertical axis represents forward-scattered light intensity (high-sensitivity) (B-FSC). In urinary particle measurements, as shown by the scattergram in FIG. 11(*c*), a range of bacteria appearance overlaps with that of mucus fibril (MUCUS), yeast-like fungi (YLC), and sperms (SPERM). However, with bacteria measurement, foreign substances such as mucus fibril and debris of erythrocytes are caused to constrict by a bacteria measurement reagent, and therefore, there is such a region where only bacteria appear independently. In addition, since measurements are made with approximately 10 times improved sensitivity compared to urinary particle measurements, small-sized bacteria can also be detected with high accuracy, thereby ensuring accurate results of bacteria measurements.

In the present embodiment, since bacteria are solely measured, reduction in reliability of the automatic classification apparatus resulting from presence of bacteria can be suppressed (bacteria are diversified in their size ranging from large ones to small ones, and there is no regularity in their distribution, they cross over on the image with other constituents such as leukocytes and erythrocytes, thereby making it difficult to facilitate correct segmentation). Even if a case judgment is made as to whether or not an instruction for re-examination (review) by a microscope, the reason for low reliability of measurement results can be attached at issuance of a re-examination instruction.

Figure 12:
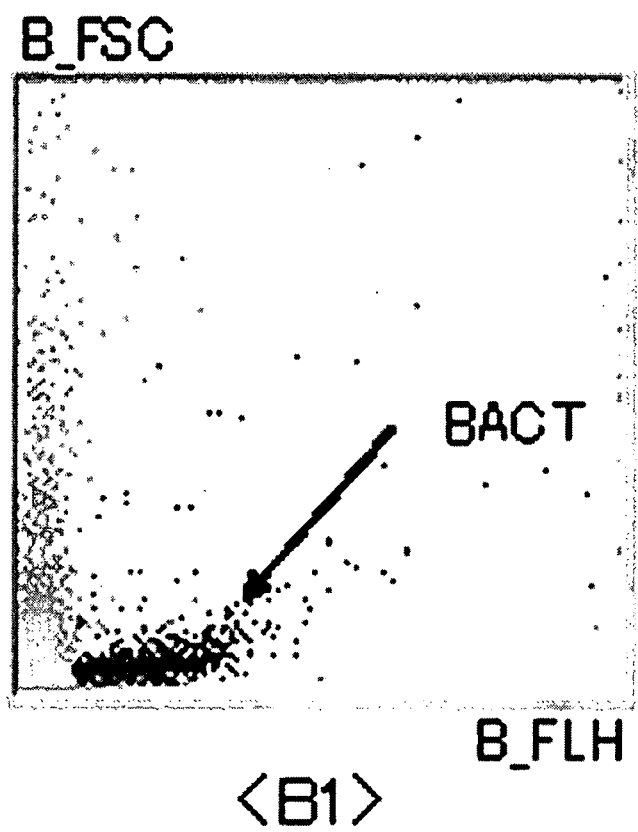
FIG. 12 is a drawing showing one example of a scattergram of a bacteria system obtained by the apparatus for analyzing particles in urine relating to one embodiment according to the present invention.
Figure 13:
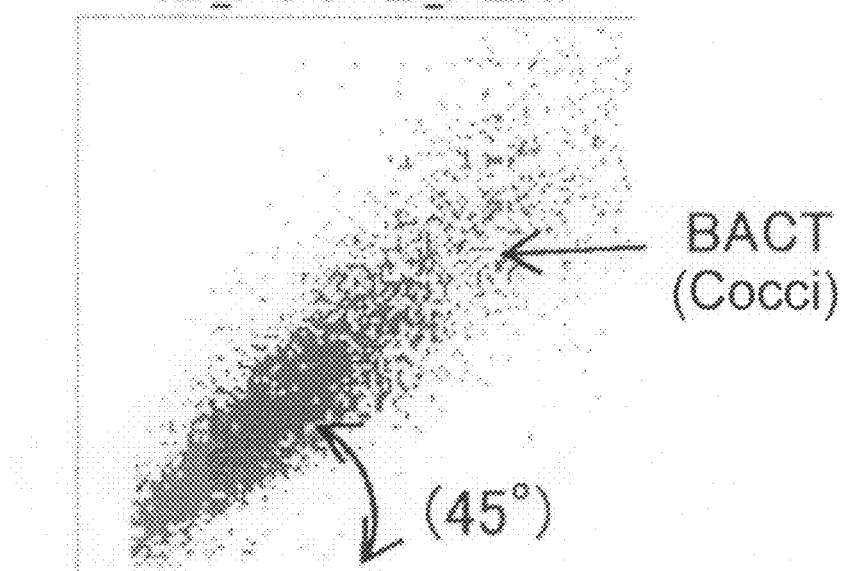
FIG. 13 is a drawing showing one example of a scattergram of a bacteria system obtained by the apparatus for analyzing particles in urine relating to one embodiment according to the present invention.

FIG. 11(*e*) shows a standard appearance region of bacteria (BACT), while the appearance region is depending on types of bacteria. FIG. 13 is an example of measurements of a sample in which a large quantity of cocci appeared and chained. In this scattergram, the region where bacteria (BACT) appeared is distributed with an angle of approximately 45° with regard to the horizontal axis (fluorescence intensity). In other words, bacteria (BACT) appeared in regions where forward-scattered light intensity (FSC) is high. With such samples, in the urinary particle measurement (SED), bacteria would appear in wider ranges, and eventually appear even in ranges, of erythrocyte appearance regions, where forward-scattered light intensity (FSC) is low. With these samples, reliability of erythrocyte measurement is low. Meanwhile, FIG. 12 shows an example of measurement of samples containing bacilli. In this scattergram, the region where bacteria (BACT) appeared is distributed with a lower angle (approximately 5 to 10 degrees) with regard to the horizontal axis (fluorescence intensity). Namely, bacteria (BACT) appeared in a region where forward-scattered light intensity (FSC) is low. With such specimens, even if bacilli is contained in a large amount, forward-scattered light intensity (FSC) in the bacteria appearance region is lower than that of the erythrocyte appearance region, and erythrocyte measurement is not affected by bacteria. Similarly, influences of bacteria on leukocyte (WBC) appearance region in the urinary particle (SED) measurement can be confirmed from bacteria distribution in the bacteria measurement (BAC). Judgment of presence or absence of influences on measurement results of other particles according to the tendency of bacteria distribution as mentioned above is carried out by algorithm analysis by the personal computer 13 (analysis section), and results of judgment are displayed on the display together with other measurement results in the Step S39.

As stated above, measurement reliability of other particles is confirmed by assuming bacteria appearance regions in the urinary particle (SED) measurement based on bacteria distribution obtained from bacteria measurement (BAC). Accordingly, it is possible to make judgment whether or not an instruction for re-examination (review) by a microscope should be given according to the distribution of bacteria measurement (BAC), thereby reducing false positive judgments and giving appropriate instructions for re-examinations. Furthermore, judgments of re-examination resulting from impossibility of fractionation with high-reliability could be reduced.

Further, it is possible to configure to allow for measurements of bacteria in urine when bacteria concentration in the urine is $5\times10^3$ cells/ml or more. Specifically, measurement of bacteria with concentrations as low as $5\times10^3$ cells/ml is made possible by setting the measurement time longer or by increasing the amount of measurement specimen. With the configuration in which measurement of bacteria in urine is possible when bacteria concentration in the urine is $5\times10^3$ cells/ml or more, bacteria measurement with sensitivity required for urine examination can be performed.

As shown above, in the apparatus for analyzing particles in urine relating to one embodiment according to the present invention, such a configuration is employed that a specimen is prepared for a urine sample using a first stain reagent and a second stain reagent, urinary particles containing at least erythrocytes are measured by a first measurement means, and bacteria are measured by a second measurement means. Therefore, it is now possible to make measurements with high accuracy by one analysis apparatus urinary particles containing at least erythrocytes and bacteria, respectively.

The optical detecting section of the apparatus for analyzing particles in urine relating to the present embodiment is configured so that receiving of forward-scattered light and side-scattered light emitted by the specimen is possible and the first measurement means is capable of measuring urinary particles based on both scattered lights. Therefore, it becomes possible, by using side-scattered light, to distinguish, for example, epithelial cells and leukocytes, or epithelial cells and bacteria, thereby improving accuracy of automatic classification (for example, false positive judgments are reduced) and at the same time, reducing the number of specimens to be subjected to re-examination under a microscope.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A method, intended for use in analyzing particles in urine, comprising:

distributing a urine sample into a first aliquot and a second aliquot;

preparing a first specimen by mixing the first aliquot and a first stain reagent;

preparing a second specimen by mixing the second aliquot and a second stain reagent which is different from the first stain reagent;

irradiating light to the first specimen, and detecting first scattered light and first fluorescence emitted from the first specimen;

irradiating light to the second specimen, and detecting second scattered light and second fluorescence emitted from the second specimen;

measuring particles in urine, the particles containing at least erythrocytes, based on the first scattered light and the first fluorescence detected from the one or more specimen; and measuring bacteria in urine, based on the second scattered light and the second fluorescence detected from the second specimen.

2. The method of claim 1, further comprising a step for judging effects of bacteria in results of the measuring of particles in urine, based on results of the measuring of bacteria in urine.

3. The method of claim 1, wherein:
    forward-scattered light and side-scattered light emitted from the specimen are detected from the first specimen; and
    the measuring of particles in urine is based on the detected forward-scattered light and the detected side-scattered light.

4. The method of claim 1, wherein the first stain reagent contains a dye for staining membrane and the second stain reagent contains a dye for staining nucleus.

5. The method of claim 1, wherein in preparing the second specimen, a surfactant is mixed with the second aliquot.

6. The method of claim 5, wherein the detecting of the second scattered light and the second fluorescence emitted from the second specimen is executed after the detecting of the first scattered light and the first fluorescence emitted from the first specimen.

7. The method of claim 2, wherein in preparing the second specimen, a temperature of the second specimen is regulated to a temperature higher than the temperature of the first specimen.

8. A method, intended for use in analyzing particles in urine, for measuring bacteria contained in urine and urinary particles containing at least erythrocytes comprising:
    a) distributing a urine sample to a first aliquot and a second aliquot;
    b) preparing a first specimen for measurement of urinary particles, the particles containing at least erythrocytes, by mixing the first aliquot and a first stain reagent;
    c) preparing a second specimen for measurement of bacteria by mixing the second aliquot and a second stain reagent which is different from the first stain reagent;
    d) detecting first scattered light and first fluorescence emitted from the first specimen by irradiating light to the first specimen; and
    e) detecting second scattered light and second fluorescence emitted from the second specimen by irradiating light to the second specimen.

9. A method, intended for use in analyzing particles in urine, comprising:
    distributing a urine sample into a first aliquot and a second aliquot;
    preparing a first specimen by mixing the first aliquot and a first stain reagent;
    preparing a second specimen by mixing the second aliquot and a second stain reagent which is different from the first stain reagent;
    irradiating light to the first specimen, and detecting first scattered light and first fluorescence emitted from the first specimen;
    irradiating light to the second specimen, and detecting second scattered light and second fluorescence emitted from the second specimen;
    measuring particles in urine, the particles containing at least erythrocytes, based on the first scattered light and the first fluorescence detected from the first specimen;
    measuring bacteria in urine, based on the second scattered light and the second fluorescence detected from the second specimen;
    displaying a first scattergram showing a distribution of at least erythrocytes based on a result of the measuring particles in urine; and
    displaying a second scattergram showing a distribution of at least bacteria based on a result of the measuring bacteria in urine.

* * * * *